(12) United States Patent
Park et al.

(10) Patent No.: US 12,027,668 B2
(45) Date of Patent: Jul. 2, 2024

(54) NON-AQUEOUS ELECTROLYTE SOLUTION FOR LITHIUM SECONDARY BATTERY AND LITHIUM SECONDARY BATTERY INCLUDING THE SAME

(71) Applicant: LG Energy Solution, Ltd., Seoul (KR)

(72) Inventors: Sung Guk Park, Daejeon (KR); Chul Haeng Lee, Daejeon (KR); Jeong Woo Oh, Daejeon (KR); Byung Chun Park, Daejeon (KR); Hyung Tae Kim, Daejeon (KR); Young Mi Seo, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 0 days.

(21) Appl. No.: 18/269,992

(22) PCT Filed: Aug. 18, 2022

(86) PCT No.: PCT/KR2022/012370
§ 371 (c)(1),
(2) Date: Jun. 28, 2023

(87) PCT Pub. No.: WO2023/022544
PCT Pub. Date: Feb. 23, 2023

(65) Prior Publication Data
US 2023/0395855 A1 Dec. 7, 2023

(30) Foreign Application Priority Data
Aug. 20, 2021 (KR) .......................... 10-2021-0110204

(51) Int. Cl.
| | | |
|---|---|---|
| H01M 10/0567 | (2010.01) | |
| C07D 231/12 | (2006.01) | |
| H01M 4/36 | (2006.01) | |
| H01M 4/38 | (2006.01) | |
| H01M 4/48 | (2010.01) | |
| H01M 4/505 | (2010.01) | |
| H01M 4/525 | (2010.01) | |
| H01M 4/587 | (2010.01) | |
| H01M 10/0568 | (2010.01) | |
| H01M 10/0569 | (2010.01) | |
| H01M 10/42 | (2006.01) | |
| H01M 4/02 | (2006.01) | |

(52) U.S. Cl.
CPC ...... *H01M 10/0567* (2013.01); *C07D 231/12* (2013.01); *H01M 4/364* (2013.01); *H01M 4/386* (2013.01); *H01M 4/483* (2013.01); *H01M 4/505* (2013.01); *H01M 4/525* (2013.01); *H01M 4/587* (2013.01); *H01M 10/0568* (2013.01); *H01M 10/0569* (2013.01); *H01M 10/4235* (2013.01); *H01M 2004/027* (2013.01); *H01M 2004/028* (2013.01); *H01M 2300/0037* (2013.01)

(58) Field of Classification Search
None
See application file for complete search history.

(56) References Cited

U.S. PATENT DOCUMENTS

| | | |
|---|---|---|
| 5,705,656 A | 1/1998 | Ono |
| 2003/0091905 A1 | 5/2003 | Nobuta et al. |
| 2005/0135045 A1 | 6/2005 | Nobuta et al. |
| 2008/0261113 A1 | 10/2008 | Huang et al. |
| 2009/0246625 A1 | 10/2009 | Lu |
| 2011/0052999 A1 | 3/2011 | Lee et al. |
| 2013/0230770 A1 | 9/2013 | Oya et al. |
| 2014/0342239 A1 | 11/2014 | Lee et al. |
| 2022/0123297 A1 | 4/2022 | Lee et al. |

FOREIGN PATENT DOCUMENTS

| | | |
|---|---|---|
| CN | 108270034 A | 7/2018 |
| CN | 109786831 A | 5/2019 |
| EP | 0749963 A1 | 12/1996 |
| JP | H05251089 A | 9/1993 |
| JP | 2003123834 A | 4/2003 |
| JP | 2005216490 A | 8/2005 |
| JP | 2007291007 A | 11/2007 |
| KR | 20030061219 A | 7/2003 |
| KR | 20100104799 A | 9/2010 |
| KR | 101013328 B1 | 2/2011 |
| KR | 101525628 B1 | 6/2015 |
| KR | 20160009952 A | 1/2016 |
| KR | 20200114403 A | 10/2020 |
| WO | 2009120872 A2 | 10/2009 |
| WO | 2012-067102 A1 | 5/2012 |

OTHER PUBLICATIONS

International Search Report for PCT/KR2022/012370 dated Nov. 18, 2022. 3 pages.
Extended European Search Report for Application No. 22858781.2 dated Jan. 31, 2024. 6 pgs.

*Primary Examiner* — Laura Weiner
(74) *Attorney, Agent, or Firm* — Lerner David LLP

(57) ABSTRACT

A non-aqueous electrolyte solution for a lithium secondary battery includes a compound represented by Formula 1 as follows, a lithium salt, and an organic solvent; and a lithium secondary battery including the same are described:

[Formula 1]

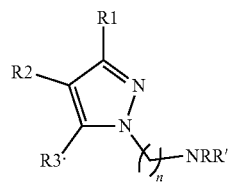

wherein R, R', R1 to R3 and n are described herein.

16 Claims, No Drawings

NON-AQUEOUS ELECTROLYTE SOLUTION FOR LITHIUM SECONDARY BATTERY AND LITHIUM SECONDARY BATTERY INCLUDING THE SAME

CROSS-REFERENCE TO RELATED APPLICATIONS

This application is a national stage entry under 35 U.S.C. § 371 of International Application No. PCT/KR2022/012370 filed on Aug. 18, 2022, which claims priority from Korean Patent Application No. 10-2021-0110204 filed on Aug. 20, 2021, all the disclosures of which are incorporated by reference herein.

TECHNICAL FIELD

The present invention relates to a non-aqueous electrolyte solution for a lithium secondary battery and a lithium secondary battery including the same.

BACKGROUND ART

A lithium secondary battery is generally prepared by a method in which, after an electrode assembly is formed by interposing a separator between a positive electrode including a positive electrode active material formed of a transition metal oxide containing lithium, and a negative electrode including a negative electrode active material capable of storing lithium ions, the electrode assembly is inserted into a battery case, a non-aqueous electrolyte solution, which becomes a medium for transferring the lithium ions, is injected thereinto, and the battery case is then sealed.

Lithium secondary batteries can be miniaturized and have high energy density and operating voltage, and thus have been applied to various fields such as mobile devices, electronic products, and electric vehicles. As the application fields of lithium secondary batteries are diversified, physical property requirements are gradually increasing, and in particular, development of lithium secondary batteries capable of being stably driven and having long life characteristics even under high temperature conditions is being required.

Meanwhile, when the lithium secondary battery is driven under high voltage and/or high temperature conditions, $PF_6^-$ anions may be thermally decomposed from a lithium salt such as $LiPF_6$ contained in the electrolyte solution to generate a Lewis acid such as $PF_5$, which reacts with moisture to generate HF. The decomposition products such as $PF_5$ and HF may not only destroy the film formed on the surface of the electrode, but may also cause decomposition reaction of the organic solvent, may react with the decomposition product of the positive electrode active material to elute transition metal ions, and the eluted transition metal ions may be electrodeposited on the negative electrode to destroy the film formed on the surface of the negative electrode.

If the electrolyte decomposition reaction is continued on the destroyed film as described above, the performance of the battery is further deteriorated, and thus the development of a secondary battery capable of maintaining excellent performance even under high voltage and high temperature conditions is being required.

DISCLOSURE OF THE INVENTION

Technical Problem

An aspect of the present invention provides a non-aqueous electrolyte solution, which can effectively remove decomposition products generated due to a lithium salt by including an aminopyrazole-based compound, and a lithium secondary battery including the same.

Technical Solution

According to an aspect of the present invention, there is provided a non-aqueous electrolyte solution including: a lithium salt; an organic solvent; and a compound represented by Formula 1 as follows.

[Formula 1]

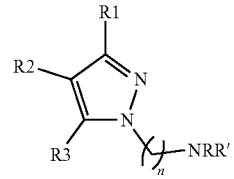

In Formula 1,
R and R' are each independently hydrogen or an alkyl group having 1 to 10 carbon atoms,
R1 to R3 are each independently hydrogen or an alkyl group having 1 to 10 carbon atoms, and
n is an integer of 1 to 10.

According to another aspect of the present invention, there is provided a lithium secondary battery including: a positive electrode including a positive electrode active material; a negative electrode including a negative electrode active material; a separator disposed between the negative electrode and the positive electrode; and the non-aqueous electrolyte solution for a lithium secondary battery.

Advantageous Effects

The non-aqueous electrolyte solution according to the present disclosure includes an aminopyrazole-based compound, which can effectively suppress the generation of decomposition products by suppressing a decomposition reaction of lithium salts, thereby preventing the destruction of an electrode film and the elution of transition metals due to the decomposition products. In addition, through this, ultimately, there may be provided a lithium secondary battery having improved electrochemical properties.

DETAILED DESCRIPTION

Hereinafter, the present invention will be described in more detail.

In general, an anion included in a lithium salt such as $LiPF_6$, which is widely used in an electrolyte solution for a lithium secondary battery, forms decomposition products such as hydrogen fluoride (HF) and $PF_5$ by thermal decomposition or moisture. These decomposition products have acidic properties and deteriorate the film or electrode surface in the battery.

Transition metals in the positive electrode are easily eluted into the electrolyte solution due to decomposition products of the electrolyte solution, structural changes of the positive electrode due to repeated charging and discharging, or the like, and the eluted transition metals are re-deposited on the positive electrode to increase the resistance of the positive electrode. In addition, when the eluted transition metals move to the negative electrode through the electrolyte solution, the eluted transition metals are electrodeposited on the negative electrode, causing destruction of a solid electrolyte interphase (SEI) film and additional electrolyte decomposition reaction, thereby causing limitations such as consumption of lithium ions and increase of resistance.

In addition, when the battery is initially activated, a protective film is formed on each of the positive electrode and the negative electrode by a reaction of the electrolyte solution, and when the film becomes unstable due to the above-described reason, additional electrolyte decomposition occurs during charging and discharging or high-temperature exposure, thereby promoting degradation of the battery and generating gas.

In order to solve the above limitations, the present inventors have found that the compound represented by Formula 1 is included in the non-aqueous electrolyte solution, and thus it is possible to reduce the decomposition reaction of the electrolyte solution and suppress elution of transition metals and gas generation. In particular, when the silicon-based negative electrode active material is used to secure high capacity, the decomposition reaction of the SEI film by the Lewis acid material generated by the decomposition of the electrolyte solution may be intensified, and when the high-Ni-based positive electrode active material is introduced, the thermal stability may be rapidly deteriorated, and the present inventors have confirmed that this limitation may be solved through the compound represented by Formula 1.

Hereinafter, various embodiments constituting the present invention will be described in more detail.

Non-Aqueous Electrolyte Solution

In one aspect, the present invention provides a non-aqueous electrolyte solution for a lithium secondary battery, the non-aqueous electrolyte solution including a lithium salt, an organic solvent, and a compound represented by Formula 1 as follows.

Hereinafter, each component will be described in detail.

(1) Compound Represented by Formula 1

The non-aqueous electrolyte solution of the present disclosure includes a compound represented by Formula 1:

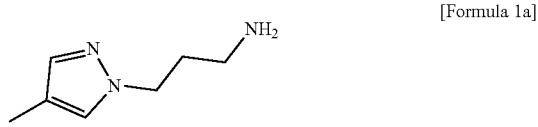

[Formula 1]

In Formula 1,

R and R' are each independently hydrogen or an alkyl group having 1 to 10 carbon atoms, R1 to R3 are each independently hydrogen or an alkyl group having 1 to 10 carbon atoms, and n is an integer of 1 to 10.

The compound represented by Formula 1 may act as a Lewis base because nitrogen elements included in pyrazole and amine groups have non-covalent electron pairs and do not participate in the delocalization. Therefore, the reaction between $PF_5$ and moisture may be suppressed through a combination reaction with $PF_5$ which is the decomposition product of the lithium salt, and thus there is an effect of suppressing the formation of HF.

Pyrazolium, which is a cation of an ionic liquid conventionally used as an electrolyte additive, has already formed an additional bond to exhibit a cationic property, and thus there is no functional group capable of being bonded to $PF_5$, and thus it is not possible to have the same effect as the compound represented by Formula 1 of the present disclosure, but there is a difference in that the compound represented by Formula 1 has a non-covalent electron pair and thus can be bonded to $PF_5$.

In an embodiment of the present invention, at least one of R1, R2 or R3 in Formula 1 may be an alkyl group having 1 to 10 carbon atoms, preferably, a methyl group.

In an embodiment of the present invention, R2 in Formula 1 may be an alkyl group having 1 to 10 carbon atoms, preferably a methyl group.

In an embodiment of the present invention, each of R1 and R3 in Formula 1 may be hydrogen.

In an embodiment of the present invention, each of R and R' in Formula 1 may be hydrogen.

In an embodiment of the present invention, n in Formula 1 may be an integer of 1 to 8, specifically, an integer of 1 to 5, and more specifically, an integer of 2 to 4.

In an embodiment of the present invention, Formula 1 may be Formula 1a below.

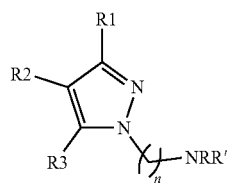

[Formula 1a]

In an embodiment of the present invention, the compound represented by Formula 1a has a shape in which an amine group is substituted at N in the ring, and thus has an advantage of higher stability compared to the structure in which an NH functional group is present in the ring.

In an embodiment of the present invention, an amount of the compound represented by Formula 1 may be in a range of 0.1 wt % to 5 wt %, preferably 0.1 wt % to 1 wt %, and more preferably 0.1 wt % to 0.5 wt % based on the total weight of the non-aqueous electrolyte solution.

When the amount of the compound represented by Formula 1 is 0.1 wt % or more, the decomposition of $PF_5$ is suppressed, and thus the effect of reducing HF may be sufficiently exhibited, when the amount is 5 wt % or less, it is preferable in terms of preventing the initial resistance increases when the battery is driven.

(2) Additive

In one embodiment, the non-aqueous electrolyte solution of the present invention may optionally further include the following additives as necessary in order to prevent the electrolyte solution from being decomposed to cause collapse of an electrode in a high-voltage environment, or further improve low-temperature high-rate discharge characteristics, high-temperature stability, overcharge protection, and a battery swelling suppression effect at high temperatures.

The additive may be at least any one selected from the group consisting of a cyclic carbonate-based compound, a halogen-substituted carbonate-based compound, a sultone-based compound, a sulfate-based compound, a phosphate-based compound, a phosphite-based compound, a borate-based compound, a nitrile-based compound, an amine-based compound, a silane-based compound, a benzene-based compound, and a lithium salt-based compound.

The cyclic carbonate-based compound may be at least any one selected from the group consisting of vinylene carbonate (VC) and vinyl ethylene carbonate (VEC), and specifically may be vinylene carbonate.

The halogen-substituted carbonate-based compound may be fluoroethylene carbonate (FEC).

The sultone-based compound is a material capable of forming a stable solid electrolyte interphase (SEI) film on the surface of a negative electrode by a reduction reaction, and may be at least any one compound selected from the group consisting of 1,3-propane sultone (PS), 1,4-butane sultone, ethene sultone, 1,3-propene sultone (PRS), 1,4-butene sultone, and 1-methyl-1,3-propene sultone, and specifically may be 1,3-propane sultone (PS).

The sulfate-based compound is a material capable of forming a stable SEI film that does not crack even during high-temperature storage by being electrically decomposed on the surface of a negative electrode, and may be at least any one selected from the group consisting of ethylene sulfate (ESa), trimethylene sulfate (TMS), and methyl trimethylene sulfate (MTMS).

The phosphate-based compound or the phosphite-based compound may be at least any one selected from the group consisting of lithium difluoro (bisoxalato)phosphate, lithium difluoro phosphate, tris(trimethylsilyl)phosphate, tris(trimethylsilyl)phosphite, tris(2,2,2-trifluoroethyl)phosphate, and tris(trifluoroethyl)phosphite.

The borate-based compound may be lithium tetraphenylborate.

The nitrile-based compound may be at least any one selected from the group consisting of succinonitrile (SN), adiponitrile (ADN), acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, 4-fluorophenylacetonitrile, ethylene glycol bis(2-cyanoethyl)ether (ASA3), 1,3,6-hexanetricarbonitrile (HTCN), 1,4-dicyano-2-butene (DCB), and 1,2,3-tris(2-cyanoethyl)propane (TCEP).

The amine-based compound may be at least any one selected group consisting of triethanolamine and ethylenediamine, and the silane-based compound may be tetravinylsilane.

The benzene-based compound may be at least any one selected from the group consisting of monofluorobenzene, difluorobenzene, trifluorobenzene, and tetrafluorobenzene.

The lithium salt-based compound is a compound different from the lithium salt included in the non-aqueous electrolyte solution, and may be at least any one compound selected from the group consisting of lithium difluoro phosphate (LiDFP; LiPO$_2$F$_2$), lithium bisoxalatoborate (LiBOB; LiB(C$_2$O$_4$)$_2$), lithium tetrafluoroborate (LiBF$_4$), and lithium difluoro (bisoxalato)phosphate (LiDFOP).

Preferably, the non-aqueous electrolyte solution according to an embodiment of the present invention may further include at least any one additive selected from vinylene carbonate (VC), vinyl ethylene carbonate (VEC), fluoroethylene carbonate (FEC), 1,3-propane sultone (PS), 1,3-propene sultone (PRS), ethylene sulfate (ESa), succinonitrile (SN), adiponitrile (ADN), ethylene glycol bis(2-cyanoethyl) ether (ASA3), 1,3,6-hexanetricarbonitrile (HTCN), 1,4-dicyano-2-butene (DCB), 1,2,3-tris(2-cyanoethyl)propane (TCEP), lithium difluoro oxalato borate (LiODFB), lithium tetrafluoroborate (LiBF$_4$), lithium difluoro(bisoxalato)phosphate (LiDFOP), or lithium difluorophosphate (LiDFP).

More preferably, the non-aqueous electrolyte solution according to an embodiment of the present invention may further include at least any one additive selected from vinylene carbonate (VC), 1,3-propane sultone (PS), ethylene sulfate (ESa), or lithium difluorophosphate (LiDFP). In this case, films are rapidly formed on the positive electrode and the negative electrode to suppress the decomposition of the compound represented by Formula 1 of the present disclosure, and thus there is an effect of increasing the residual amount of the compound capable of being bonded to PF$_5$.

Meanwhile, an amount of the additive may be in a range of 0.1 wt % to 10 wt %, preferably, 0.3 wt % to 5 wt % based on the total weight of the non-aqueous electrolyte solution. When the additive content is within the above range, there is an effect of suppressing side reactions through the formation of the films on the positive electrode and the negative electrode.

(3) Organic Solvent

The non-aqueous electrolyte solution of the present disclosure includes an organic solvent.

Various organic solvents typically used in a lithium electrolyte may be used as the organic solvent without limitation. For example, the organic solvent may be a cyclic carbonate-based solvent, a linear carbonate-based solvent, a linear ester-based solvent, a cyclic ester-based solvent, a nitrile-based solvent, or a mixture thereof, and may preferably include a mixture of a cyclic carbonate-based solvent and a linear carbonate-based solvent.

The cyclic carbonate-based solvent is a highly viscous organic solvent which may well dissociate the lithium salt in the electrolyte due to high permittivity, and may be at least any one selected from the group consisting of ethylene carbonate (EC), propylene carbonate (PC), 1,2-butylene carbonate, 2,3-butylene carbonate, 1,2-pentylene carbonate, 2,3-pentylene carbonate, and vinylene carbonate, and may preferably include ethylene carbonate (EC) or propylene carbonate (PC).

In addition, the linear carbonate-based solvent is an organic solvent having low viscosity and low permittivity, and may be at least any one selected from the group consisting of dimethyl carbonate (DMC), diethyl carbonate (DEC), dipropyl carbonate, ethyl methyl carbonate (EMC), methylpropyl carbonate, and ethylpropyl carbonate, and may preferably include ethyl methyl carbonate (EMC), dimethyl carbonate (DMC), or diethyl carbonate (DEC).

In order to prepare an electrolyte having high ionic conductivity, it is desirable to use a mixture of the cyclic carbonate-based solvent and the linear carbonate-based solvent as the organic solvent.

The linear ester-based solvent may include at any one selected from the group consisting of methyl acetate, ethyl acetate, propyl acetate, methyl propionate, ethyl propionate, propyl propionate, and butyl propionate, and may preferably be methyl propionate, ethyl propionate, or propyl propionate.

The cyclic ester-based solvent may be at least any one selected from the group consisting of γ-butyrolactone, γ-valerolactone, γ-caprolactone, σ-valerolactone, and ε-caprolactone.

The nitrile-based solvent may be at least any one selected from the group consisting of succinonitrile, acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile and 4-fluorophenylacetonitrile, and may preferably be succinonitrile.

Remainders except for the amounts of the other components except for the organic solvent, for example, the compound represented by Formula 1, the additive, and the lithium salt in the total weight of the non-aqueous electrolyte solution may all be organic solvents unless otherwise stated.

(4) Lithium Salt

The non-aqueous electrolyte solution of the present disclosure includes a lithium salt.

Any lithium salt typically used in an electrolyte for a lithium secondary battery may be used as the lithium salt without limitation, and specifically, the lithium salt may include Li$^+$ as a cation, and may include at least one selected from F$^-$, Cl$^-$, Br$^-$, I$^-$, NO$_3^-$, N(CN)$_2^-$, BF$_4^-$, ClO$_4^-$, B$_{10}$Cl$_{10}^-$, AlCl$_4^-$, AlO$_4^-$, PF$_6^-$, CF$_3$SO$_3^-$, CH$_3$CO$_2^-$, CF$_3$CO$_2^-$, AsF$_6^-$, SbF$_6^-$, CH$_3$SO$_3^-$, (CF$_3$CF$_2$SO$_2$)$_2$N$^-$, (CF$_3$SO$_2$)$_2$N$^-$, (FSO$_2$)$_2$N$^-$, BF$_2$C$_2$O$_4^-$, BC$_4$O$_8^-$, BF$_2$C$_2$O$_4$CHF—, PF$_4$C$_2$O$_4^-$, PF$_2$C$_4$O$_8^-$, PO$_2$F$_2^-$, (CF$_3$)$_2$PF$_4^-$, (CF$_3$)$_3$PF$_3^-$, (CF$_3$)$_4$PF$_2^-$, (CF$_3$)$_5$PF$^-$, (CF$_3$)$_6$P$^-$, C$_4$F$_9$SO$_3^-$, CF$_3$CF$_2$SO$_3^-$, CF$_3$CF$_2$ (CF$_3$)$_2$CO$^-$, (CF$_3$SO$_2$)$_2$CH$^-$, CF$_3$ (CF$_2$)$_7$SO$_3^-$, or SCN$^-$ as an anion.

Specifically, the lithium salt may be at least any one selected from the group consisting of LiPF$_6$, LiClO$_4$, LiBF$_4$, LiN(PSO$_2$)$_2$(LiFSI), lithium bis(trifluoromethanesulfonyl) imide (LiTFSI), lithium bis(pentafluoroethanesulfonyl)imide (LiBETI), LiSO$_3$CF$_3$, LiPO$_2$F$_2$, lithium bis(oxalate) borate (LiBOB), lithium difluoro(oxalate)borate (LiFOB), lithium difluoro(bisoxalato) phosphate (LiDFOP), lithium tetrafluoro(oxalate) phosphate (LiTFOP), and lithium fluoromalonato(difluoro) borate (LiFMDFB), and may preferably be LiPF6.

In an embodiment of the present invention, a concentration of the lithium salt in the non-aqueous organic solution containing the lithium salt and the organic solvent may be in a range of 0.5 M to 4.0 M, preferably, 0.5 M to 3.0 M, and more preferably, 0.8 M to 2.0 M. When the concentration of the lithium salt is within the above range, the effect of improving low-temperature output and cycle characteristics is sufficiently secured, and the viscosity and surface tension are prevented from being excessively increased, thereby obtaining appropriate electrolyte impregnability.

Lithium Secondary Battery

Next, a lithium secondary battery according to one aspect of the present invention will be described.

The lithium secondary battery according to the present disclosure includes a positive electrode including a positive electrode active material, a negative electrode including a negative electrode active material, a separator disposed between the positive electrode and the negative electrode, and a non-aqueous electrolyte solution, and, in this case, the non-aqueous electrolyte is the non-aqueous electrolyte solution according to the present disclosure. Since the non-aqueous electrolyte solution has been described above, a description thereof will be omitted and other components will be described below.

(1) Positive Electrode

The positive electrode according to the present disclosure may include a positive electrode active material and be prepared by coating a positive electrode collector with a positive electrode slurry containing the positive electrode active material, a binder, a conductive agent, a solvent, etc., and then drying and rolling the coated positive electrode collector.

The positive electrode collector is not particularly limited so long as it has conductivity without causing adverse chemical changes in the battery, and, for example, stainless steel; aluminum; nickel; titanium; sintered carbon; or aluminum or stainless steel of which the surface is treated with carbon, nickel, titanium, silver, or the like may be used.

The positive electrode active material is a compound capable of reversibly intercalating and deintercalating lithium, and may be at least any one selected from the group consisting of LcO(LiCoO$_2$); LNO(LiNiO$_2$); LMO (LiMnO$_2$); LiMn$_2$O$_4$, LiCoPO$_4$; LFP(LiFePO$_4$); and a lithium composite transition metal oxide including nickel (Ni), cobalt (Co), and manganese (Mn).

In an embodiment of the present invention, the positive electrode active material may have a molar ratio of nickel in the transition metal of 70 mol % or more, preferably 80 mol % or more, and more preferably 85 mol % or more.

In an embodiment of the present invention, the lithium composite transition metal oxide may be any one selected from the group consisting of LiNiCoMnO$_2$; LiNi$_{1-x-y-z}$Co$_x$M$^1_y$M$^2_z$O$_2$ (M$^1$ and M$^2$ are each independently any one selected from the group consisting of Al, Ni, Co, Fe, Mn, V, Cr, Ti, W, Ta, Mg, and Mo, and x, y, and z are each independently an atomic fraction of oxide composition elements, and 0≤x<0.5, 0≤y<0.5, 0≤z<0.5, and x+y+z=1); and a compound represented by Formula 2 as follows.

Specifically, the positive electrode active material may include a lithium composite transition metal oxide represented by Formula 2:

$$Li_{1+x}(Ni_aCo_bMn_cM_d)O_2 \qquad \text{[Formula 2]}$$

In Formula 2,

M is at least any one selected from the group consisting of W, Cu, Fe, V, Cr, Ti, Zr, Zn, Al, In, Ta, Y, La, Sr, Ga, Sc, Gd, Sm, Ca, Ce, Nb, Mg, B, and Mo, 1+x, a, b, c, and d are each independently an atomic fraction of elements, and −0.2≤x≤0.2, 0.50≤a<1, 0<b≤0.3, 0<c≤0.3, 0≤d≤0.1, and a+b+c+d=1.

1+x above represents a molar ratio of lithium in a lithium composite transition metal oxide, and x may satisfy −0.1≤x≤0.2, or 0≤x≤0.2. When the molar ratio of lithium satisfies the above range, the crystal structure of the lithium composite transition metal oxide may be stably formed.

a above represents a molar ratio of nickel among all metals excluding lithium in the lithium composite transition metal oxide, and may satisfy 0.60≤a<1, 0.70≤a<1, 0.80≤a<1, or 0.85≤a<1. When the molar ratio of nickel satisfies the above range, high energy density may be exhibited and high capacity may be achieved.

b above represents a molar ratio of cobalt among all metals excluding lithium in the lithium composite transition metal oxide, and may satisfy 0<b≤0.25, 0<b≤0.20, 0<b≤0.15, or 0<b≤0.10. When the molar ratio of cobalt satisfies the above range, good resistance characteristics and output characteristics may be achieved.

c above represents a molar ratio of manganese among all metals excluding lithium in the lithium composite transition metal oxide, and may satisfy 0<c≤0.25, 0<c≤0.20, 0<c≤0.15, or 0<c≤0.10. When the molar ratio of manganese satisfies the above range, the structural stability of the positive electrode active material is exhibited excellent.

In an embodiment of the present invention, the lithium composite transition metal oxide may include at least one doping element selected from W, Cu, Fe, V, Cr, Ti, Zr, Zn, Al, In, Ta, Y, La, Sr, Ga, Sc, Gd, Sm, Ca, Ce, Nb, Mg, B, or Mo. In other words, d above representing the molar ratio of the doping element in all metals excluding lithium in the lithium composite transition metal oxide may satisfy 0<d≤0.10, 0<d≤0.08, 0<d≤0.05, or 0<d≤0.03.

More specifically, the lithium composite transition metal oxide may be at least any one selected from the group consisting of $Li(Ni_{0.6}Mh_{0.2}Co_{0.2})O_2$, $Li(Ni_{0.7}Mn_{0.15}Co_{0.15})O_2$, $Li(Ni_{0.8}Mh_{0.1}Co_{0.1})O_2$, and $Li(Ni_{0.9}Mh_{0.03}Co_{0.06}Al_{0.01})O_2$.

The positive electrode active material may be included in an amount of 80 wt % to 99 wt %, specifically, 90 wt % to 99 wt % based on the total weight of the solid content in the positive electrode slurry. In this case, when the amount of the positive electrode active material is 80 wt % or less, since energy density is reduced, capacity may be reduced.

The binder is a component that assists in the binding between the active material and the conductive agent and in the binding with the current collector, and may be commonly added in an amount of 1 wt % to 30 wt % based on the total weight of the solid content in the positive electrode slurry. Examples of the binder may be polyvinylidene fluoride, polyvinyl alcohol, carboxymethylcellulose (CMC), starch, hydroxypropylcellulose, regenerated cellulose, polyvinylpyrrolidone, polytetrafluoroethylene, polyethylene, polypropylene, an ethylene-propylene-diene monomer, a sulfonated ethylene-propylene-diene monomer, a styrene-butadiene rubber, a fluoro rubber, or various copolymers thereof.

In addition, the conductive agent is a material providing conductivity without causing adverse chemical changes in the battery, and may be added in an amount of 0.5 wt % to 20 wt % based on the total weight of the solid content in the positive electrode slurry.

For example, the conductive agent may be at least any one selected from carbon black such as acetylene black, Ketjen black, channel black, furnace black, lamp black, or thermal black; graphite powder such as natural graphite, artificial graphite, or graphite; conductive fibers such as carbon fibers or metal fibers; conductive powder such as fluorocarbon powder, aluminum powder, or nickel powder; conductive whiskers such as zinc oxide whiskers or potassium titanate whiskers; conductive metal oxide such as titanium oxide; or a conductive material such as polyphenylene derivatives.

Furthermore, the solvent of the positive electrode slurry may include an organic solvent, such as N-methyl-2-pyrrolidone (NMP), and may be used in an amount such that desirable viscosity is obtained when the positive electrode active material, the binder, and the conductive agent are included. For example, the solvent may be included in an amount such that a concentration of the solid content in the positive electrode slurry containing the positive electrode active material, the binder, and the conductive agent is 40 wt % to 90 wt %, preferably, 50 wt % to 80 wt %.

(2) Negative Electrode

The negative electrode according to the present disclosure may include a negative electrode active material and be prepared by coating a negative electrode collector with a negative electrode slurry containing the negative electrode active material, a binder, a conductive agent, a solvent, etc., and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper; stainless steel; aluminum; nickel; titanium; sintered carbon; copper or stainless steel that is surface-treated with one of carbon, nickel, titanium, silver, or the like; an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, and a non-woven fabric body.

In an embodiment of the present invention, the negative electrode active material may include a silicon-based material, and the silicon-based material may be at least any one selected from the group consisting of Si, $SiO_x$ (0<x<2), and a Si—Y alloy (Y is an element selected from an alkali metal, an alkaline earth metal, a Group 13 element, a Group 14 element, a transition metal, a rare earth element, or a combination thereof, and cannot be Si), and preferably SiO.

The capacity of the silicon-based negative electrode active material is about 10 times higher than that of graphite, and thus mass loading ($mg \cdot cm^{-2}$) is lowered, thereby improving fast charging performance of the battery. However, there is a limitation in that the lithium ion loss rate due to the irreversible reaction is high and the volume change is large, thereby adversely affecting the life, and this limitation may be solved by applying the above-described non-aqueous electrolyte solution. However, a negative electrode containing the silicon-based negative electrode active material contains more oxygen-rich (O-rich) components in the SEI film than a graphite negative electrode, and the SEI film containing the O-rich components tends to be more easily decomposed when a Lewis acid, such as HF or $PF_5$, is present in the electrolyte. Thus, with respect to the negative electrode containing the silicon-based negative electrode active material, there is a need to suppress the formation of the Lewis acid, such as HF and $PF_5$, or scavenge the formed Lewis acid in order to stably maintain the SEI film. Since the non-aqueous electrolyte solution according to the present disclosure includes the compound represented by Formula 1, which can suppress the generation of Lewis acid or remove the generated Lewis acid, it is possible to effectively solve the limitation of the SEI film decomposition accompanying the use of the negative electrode containing the silicon-based active material.

In an embodiment of the present invention, the silicon-based material may be included in an amount of 1 wt % to 20 wt %, preferably, 5 wt % to 15 wt % based on the total weight of the negative electrode active material. When the silicon-based material is included in the above range, there is an effect of increasing the capacity of the negative electrode and improving the fast charging performance.

In one embodiment, the negative electrode active material of the present invention may further include a carbon-based material; a metal or an alloy of lithium and the metal; a metal composite oxide; a material which may be doped and undoped with lithium; a lithium metal; or a transition metal oxide in addition to the silicon-based material.

As the carbon-based material, a carbon-based negative electrode active material generally used in a lithium ion secondary battery may be used without particular limitation, and as a typical example, crystalline carbon, amorphous carbon, or a mixture thereof may be used. Examples of the crystalline carbon may include graphite such as irregular, planar, flaky, spherical, or fibrous natural graphite or artificial graphite, and examples of the amorphous carbon may include soft carbon (low-temperature sintered carbon) or hard carbon, mesophase pitch carbide, sintered cokes, or the like.

As the metal or the alloy of lithium and the metal, a metal selected from the group consisting of Cu, Ni, Na, K, Rb, Cs, Fr, Be, Mg, Ca, Sr, Si, Sb, Pb, In, Zn, Ba, Ra, Ge, Al, and Sn, or an alloy of lithium and the metal may be used.

As the metal composite oxide, at least any one selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3$ ($0 \leq x \leq 1$), $Li_xWO_2$ ($0 \leq x \leq 1$), and $Sn_xMe_{1-x}Me'_yO_z$ (where: Me is Mn, Fe, Pb, or Ge; Me' is Al, B, P, Si, Groups I, II and III elements of the periodic table, or halogen; $0<x \leq 1$; $1 \leq y=3$; and $1 \leq z \leq 8$) may be used.

The material which may be doped and undoped with lithium may include Sn, $SnO_2$, Sn—Y (wherein Y above is an element selected from the group consisting of an alkali metal, an alkaline earth metal, a Group 13 element, a Group 14 element, a transition metal, a rare earth element, and a combination thereof, and is not Sn), or the like.

In Si—Y and Sn—Y above, the element Y may be at least any one selected from the group consisting of Mg, Ca, Sr, Ba, Ra, Sc, Y, Ti, Zr, Hf, Rf, V, Nb, Ta, db (dubnium), Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ge, P, As, Sb, Bi, S, Se, Te, and Po.

Examples of the transition metal oxide may include lithium-containing titanium composite oxide (LTO), vanadium oxide, lithium vanadium oxide, or the like.

The negative electrode active material may be included in an amount of 80 wt % to 99 wt % based on the total weight of solid content in the negative electrode slurry.

The binder is a component that assists in the binding among the conductive agent, the active material, and the current collector, and is commonly added in an amount of 1 wt % to 30 wt % based on the total weight of the solid content in the negative electrode slurry. Examples of the binder may include polyvinylidene fluoride, polyvinyl alcohol, carboxymethylcellulose (CMC), starch, hydroxypropylcellulose, regenerated cellulose, polyvinylpyrrolidone, polytetrafluoroethylene, polyethylene, polypropylene, an ethylene-propylene-diene monomer, a sulfonated ethylene-propylene-diene monomer, a styrene-butadiene rubber, a fluoro rubber, various copolymers thereof, or the like.

The conductive agent is a component for further improving the conductivity of the negative electrode active material, and may be added in an amount of 0.5 wt % to 20 wt % based on the total weight of the solid content in the negative electrode slurry. The conductive agent is not particularly limited as long as it has conductivity without causing adverse chemical changes in the battery, and, for example, may be at least any one selected from carbon black such as acetylene black, Ketjen black, channel black, furnace black, lamp black, or thermal black; graphite powder such as natural graphite, artificial graphite, or graphite; conductive fibers such as carbon fibers or metal fibers; conductive powder such as fluorocarbon powder, aluminum powder, or nickel powder; conductive whiskers such as zinc oxide whiskers or potassium titanate whiskers; conductive metal oxide such as titanium oxide; or a conductive material such as polyphenylene derivatives.

The solvent of the negative electrode slurry may include water; or an organic solvent, such as NMP or alcohol, and may be used in an amount such that desirable viscosity is obtained when the negative electrode active material, the binder, the conductive agent, and the like are included. For example, the solvent may be included in an amount such that a concentration of the solid content in the slurry including the negative electrode active material, the binder, and the conductive agent is 30 wt % to 80 wt %, preferably, 40 wt % to 70 wt %.

(3) Separator

The lithium secondary battery according to the present disclosure includes a separator between the positive electrode and the negative electrode.

The separator separates the negative electrode and the positive electrode and provides a movement path of lithium ions, and any separator may be used as the separator without particular limitation as long as it is typically used in a lithium secondary battery, and particularly, a separator having excellent wettability of the electrolyte and excellent stability as well as low resistance to the transfer of electrolyte ions is preferable.

Specifically, a porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer; or a laminated structure having two or more layers thereof may be used as the separator. Also, a typical porous nonwoven fabric, for example, a nonwoven fabric formed of high melting point glass fibers or polyethylene terephthalate fibers may be used. Furthermore, a coated separator including a ceramic component or a polymer material may be used to secure heat resistance or mechanical strength, and the separator having a single layer or multilayer structure may be used.

The lithium secondary battery according to the present disclosure as described above may be useful for portable devices, such as mobile phones, notebook computers, and digital cameras, electric cars such as hybrid electric vehicles (HEVs), and the like.

Thus, according to another embodiment of the present invention, a battery module including the lithium secondary battery as a unit cell and a battery pack including the battery module are provided.

The battery module or the battery pack may be used as a power source of at least one medium or large sized device of a power tool; electric cars including an electric vehicle (EV), a hybrid electric vehicle, a plug-in hybrid electric vehicle (PHEV); or a power storage system.

A shape of the lithium secondary battery of the present disclosure is not particularly limited, but a cylindrical type using a can, a prismatic type, a pouch type, a coin type, or the like may be used.

The lithium secondary battery according to the present disclosure may not only be used in a battery cell that is used as a power source of a small device, but may also be preferably used as a unit cell in a medium-and-large-sized battery module including a plurality of battery cells.

Hereinafter, the present invention will be described in detail with reference to specific examples.

EXAMPLES

Example 1

(Preparation of Non-aqueous Electrolyte Solution)

A non-aqueous organic solution was prepared by mixing ethylene carbonate (EC) and ethyl methyl carbonate (EMC) in a volume ratio of 30:70 and then dissolving $LiPF_6$ in the mixture so as to have a concentration of 1.0 M. A non-aqueous electrolyte solution (100 wt %) was prepared by mixing 0.5 wt % of the compound represented by Formula 1a and the non-aqueous organic solution as a remainder.

(Preparation of Lithium Secondary Battery)

$Li(Ni_{0.9}Mn_{0.03}Co_{0.06}Al_{0.01})O_2$ as a positive electrode active material, a conductive agent (carbon black), and a binder (polyvinylidene fluoride) were added to N-methyl-2-pyrrolidone (NMP) at a weight ratio of 97.6:0.8:1.6 to prepare a positive electrode slurry (solid content: 60 wt %). A 13.5 μm thick aluminum (Al) thin film, as a positive electrode collector, was coated with the positive electrode slurry, dried, and then roll-pressed to prepare a positive electrode.

A negative electrode active material (graphite:SiO=90.0:10.0 weight ratio), a binder (SBR-CMC), and a conductive agent (carbon black) were added in a weight ratio of 97.6:0.8:1.6 to water, which is a solvent, to prepare a negative electrode slurry (solid content: 60 wt %). A 6 μm thick copper (Cu) thin film, as a negative electrode collector, was coated with the negative electrode slurry, dried, and then roll-pressed to prepare a negative electrode.

An electrode assembly was prepared by sequentially stacking the positive electrode, a polyolefin-based porous separator coated with inorganic particles ($Al_2O_3$), and the negative electrode.

The electrode assembly was accommodated in a pouch-type battery case, and the prepared non-aqueous electrolyte solution was injected thereinto to prepare a lithium secondary battery.

Example 2

A lithium secondary battery was prepared in the same manner as in Example 1 except that the amount of the compound represented by Formula 1a is changed to 0.3 wt % and 0.5 wt % of vinylene carbonate (VC) is further added in the preparation of the non-aqueous electrolyte solution.

Comparative Example 1

A lithium secondary battery was prepared in the same manner as in Example 1 except that the compound represented by Formula 1a was not added in the preparation of the non-aqueous electrolyte solution.

Comparative Example 2

A lithium secondary battery was prepared in the same manner as in Example 2 except that the compound represented by Formula 1a was not added in the preparation of the non-aqueous electrolyte solution.

Experimental Example 1: HF Content Measurement after High-Temperature Storage After the non-aqueous electrolyte solutions prepared in Example 1 and Comparative Example 1 were left at 60° C. for 4 weeks, the hydrogen fluoride (HF) content in the electrolyte solutions was measured in ppm by acid-base neutralization titration. Metrohm 785 DMP Titrino was used as measurement equipment, and 0.1 N of sodium hydroxide standard solution was used as the titration sample. Specifically, after about 100 mL of cold tertiary distilled water was injected into a 250-mL beaker having a magnetic bar, the beaker was placed in an ice bath, waited until it reached 3° C., and then, when it reached 3° C., an electrode and a dosing tube were immersed in the beaker and stirred. After each of the non-aqueous electrolyte solutions of Example 1 and Comparative Example 1 was added in the stirred state, the accurate weight of the sample was input to start titration, and the concentration of HF measured through titration was shown in Table 1 below.

TABLE 1

| | HF after high-temperature storage (ppm) |
|---|---|
| Example 1 | 4.43 |
| Comparative Example 1 | 67.1 |

From the results of Table 1, it may be confirmed that the concentration of HF in the non-aqueous electrolyte solution in Example 1 including the compound represented by Formula 1a was lower than that in the non-aqueous electrolyte solution in Comparative Example 1 not including the compound represented by Formula 1a. That is, it may be seen that the compound represented by Formula 1a of the present application suppresses the decomposition reaction of the lithium salt in the electrolyte solution so that the concentration of HF, which is the decomposition product, is lowered.

Experimental Example 2: High-temperature Storage Evaluation

After each of the lithium secondary batteries prepared in Example 2 and Comparative Example 2 was activated at a CC of 0.1 C, degassing was performed.

Subsequently, each secondary battery was charged at a CC of 0.33 C to 4.20 V under a constant current-constant voltage (CC-CV) condition at 25° C., and then stored at 60° C. for 8 weeks. Thereafter, amounts of gases generated in the lithium secondary batteries were measured, and the results are shown in Table 2 below.

TABLE 2

| | Amount of $CO_2$ generated (μL) | Amount of CO generated (μL) | Amount of hydrocarbon generated (μL) | Total (μL) |
|---|---|---|---|---|
| Example 2 | 945 | 71 | 605 | 1,621 |
| Comparative Example 2 | 1,160 | 70 | 749 | 1,979 |

From the results of Table 2, it may be confirmed that the amounts of gases generated in the battery in Example 2 including the compound represented by Formula 1a was much less than that in the battery in Comparative Example 2 not including the compound represented by Formula 1a. That is, when the electrolyte solution including the compound represented by Formula 1a is used, it may be seen that the amounts of gases generated, which are factors that deteriorate the performance of the battery and the safety after high-temperature storage, are reduced.

The invention claimed is:

1. A non-aqueous electrolyte solution for a lithium secondary battery, the non-aqueous electrolyte solution comprising a lithium salt, an organic solvent, and an additive represented by Formula 1:

[Formula 1]

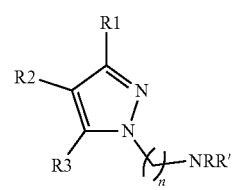

wherein, in Formula 1,

R and R' are each independently hydrogen or an alkyl group having 1 to 10 carbon atoms, R1 to R3 are each independently hydrogen or an alkyl group having 1 to 10 carbon atoms, and n is an integer of 1 to 10, wherein the additive is included in an amount of 0.1 wt % to 5 wt % based on a total weight of the non-aqueous electrolyte solution.

2. The non-aqueous electrolyte solution of claim 1, wherein the additive is represented by Formula 1a:

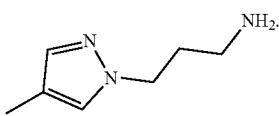

[Formula 1a]

3. The non-aqueous electrolyte solution of claim 1, wherein at least one of R1, R2 or R3 in Formula 1 is an alkyl group having 1 to 10 carbon atoms.

4. The non-aqueous electrolyte solution of claim 1, wherein R2 in Formula 1 is an alkyl group having 1 to 10 carbon atoms.

5. The non-aqueous electrolyte solution of claim 1, wherein each of R and R' in Formula 1 is hydrogen.

6. The non-aqueous electrolyte solution claim 1, wherein the additive is included in an amount of 0.1 wt % to 1 wt % based on a-the total weight of the non-aqueous electrolyte solution.

7. The non-aqueous electrolyte solution of claim 1, further comprising a second additive selected from vinylene carbonate, 1,3-propane sultone, ethylene sulfate, or-lithium difluoro phosphate, or a mixture thereof, wherein the second additive is included in an amount of 0.1 wt % to 10 wt % based on the total weight of the non-aqueous electrolyte solution.

8. The non-aqueous electrolyte solution of claim 1, wherein the organic solvent comprises a mixture of a cyclic carbonate-based solvent and a linear carbonate-based solvent.

9. The non-aqueous electrolyte solution of claim 1, wherein n in Formula 1 is an integer of 1 to 5.

10. The non-aqueous electrolyte solution of claim 1, wherein the lithium salt comprises at least one selected from $LiPF_6$, $LiClO_4$, $LiBF_4$, $LiN(FSO_2)_2$, lithium bis(trifluoromethanesulfonyl)imide, lithium bis(pentafluoroethanesulfonyl)imide, $LiSO_3CF_3$, $LiPO_2F_2$, lithium bis(oxalate) borate, lithium difluoro(oxalate)borate, lithium difluoro (bisoxalato) phosphate, lithium tetrafluoro(oxalate) phosphate, or lithium fluoromalonato(difluoro) borate.

11. A lithium secondary battery comprising:
a positive electrode including a positive electrode active material;
a negative electrode including a negative electrode active material;
a separator disposed between the positive electrode and the negative electrode; and
the non-aqueous electrolyte solution of claim 1.

12. The lithium secondary battery of claim 11, wherein the positive electrode active material comprises a lithium composite transition metal oxide represented by Formula 2:

$$Li_{1+x}x(Ni_aCo_bMn_cM_d)O_2$$ [Formula 2]

wherein, in Formula 2,

M is at least one selected from W, Cu, Fe, V, Cr, Ti, Zr, Zn, Al, In, Ta, Y, La, Sr, Ga, Sc, Gd, Sm, Ca, Ce, Nb, Mg, B, or Mo, 1+x, a, b, c, and d are each independently an atomic fraction of Li, Ni, Co, Mn and M, respectively, and $-0.2 \leq x \leq 0.2$, $0.50 \leq a < 1$, $0 < b \leq 0.3$, $0 < c \leq 0.3$, $0 \leq d \leq 0.1$, and $a+b+c+d=1$.

13. The lithium secondary battery of claim 12, wherein the lithium composite transition metal oxide is at least one selected from $Li(Ni_{0.6}Mn_{0.2}Co_{0.2})O_2$, $Li(Ni_{0.7}Mn_{0.15}Co_{0.15})O_2$, $Li(Ni_{0.8}Mn_{0.1}Co_{0.1})O_2$, or $Li(Ni_{0.9}Mn_{0.03}Co_{0.06}Al_{0.01})O_2$.

14. The lithium secondary battery of claim 11, wherein the positive electrode active material has a molar ratio of nickel among transition metals of 70 mol % or to less than 100 mol %.

15. The lithium secondary battery of claim 11, wherein the negative electrode active material comprises a silicon-based material and a carbon-based material, wherein the silicon-based material is included in an amount of 1 wt % to 20 wt % based on a total weight of the negative electrode active material.

16. The lithium secondary battery of claim 15, wherein the silicon-based material is at least one selected from Si, $SiO_x$ ($0<x<2$), or a Si—Y alloy, wherein Y is an element selected from an alkali metal, an alkaline earth metal, a Group 13 element, a Group 14 element, a transition metal, a rare earth element, or a combination thereof, and is not Si.

* * * * *